United States Patent [19]

LeFevre

[11] 4,103,686
[45] Aug. 1, 1978

[54] DUAL VALVE ASSEMBLY
[75] Inventor: Robert J. LeFevre, Bethlehem, Pa.
[73] Assignee: Burron Medical Products, Inc., Bethlehem, Pa.
[21] Appl. No.: 782,411
[22] Filed: Mar. 29, 1977
[51] Int. Cl.² .............................................. A61M 5/00
[52] U.S. Cl. ................................ 128/214 R; 128/227; 128/274; 137/211; 137/614.21; 251/139
[58] Field of Search ............ 128/214 R, 214 C, 214.2, 128/227, 274; 137/211, 614.11, 614.2, 614.21; 251/139

[56] References Cited

U.S. PATENT DOCUMENTS

| | | | |
|---|---|---|---|
| 2,538,662 | 1/1951 | Abbott | 128/214 R |
| 3,886,937 | 6/1975 | Bobo et al. | 128/214 R |
| 3,890,968 | 6/1975 | Pierce et al. | 128/214 R |
| 4,000,740 | 1/1977 | Mittleman | 128/214 R |
| 4,005,710 | 2/1977 | Zeddies et al. | 128/214 R |
| 4,038,981 | 8/1977 | LeFevre et al. | 128/214 E |

*Primary Examiner*—Dalton L. Truluck
*Attorney, Agent, or Firm*—Shoemaker and Mattare, Ltd.

[57] ABSTRACT

A dual valve assembly for intravenous infusions from multiple parenteral fluid sources, the assembly controlling both forward and reverse flow through a flow line includes normally seated first and second valves mounted for movement toward and away from respective valve seats to control flow in a first direction, one of said valves being opened in response to opening movement of the other valve and said one valve including a second seat and movable into closing relationship on its second seat in response to reverse flow to thus prevent reverse flow through the assembly.

10 Claims, 5 Drawing Figures

DUAL VALVE ASSEMBLY

BACKGROUND OF THE INVENTION

This invention relates to a valve means which includes multiple valve members each having a first valve seat upon which the valve members are normally seated to insure positive shut-off of flow in a first direction through the assembly and wherein one of the valve members has a second seat against which the other valve member seats to prevent reverse flow through the assembly.

More particularly, the present invention relates to a dual valve assembly for use in intravenous administration sets to control flow therethrough in instances wherein more than one fluid is to be administered to a patient, as by means of multiple sources of fluids connected with a Y-connector or the like supplying the fluids to a common needle or cannula. In such arrangements, provision normally is made for interrupting flow from one of the sources while flow occurs from the other of the sources. Prior art arrangements for effecting this flow control usually involve various clamps and valve assemblies which must be manually operated in order to obtain the proper and necessary flow control. This, of course, requires the attention of a nurse or other attendant who must be present when one of the fluid sources is depleted so that the attendant can manipulate the valves to begin supplying fluid from the other source and thus prevent introduction of air into the vein of the patient.

Examples of some prior art arrangements are shown in U.S. Pat. No. 3,886,937 and in applicant's prior copending application Ser. No. 703,907.

In the present invention, the valve assembly is constructed of a minumum number of parts assembled together to provide a valve housing defining a first valve seat therein and having a first valve member reciprocable toward and away from the first valve seat. The first valve member is normally seated under the action of gravity and is moved to open position by an electromagnet positioned exteriorly of the housing. A valve stop member is spaced a predetermined distance from the seat to limit opening movement of the valve and a second valve member is mounted in the housing spaced upstream from the first valve member and is normally seated on a second valve seat under the action of gravity and of fluid pressure thereabove for preventing forward flow through the assembly. When the first valve member is opened by energization of the electromagnet, an elongate valve actuating rod is engaged by the first valve member and moved upwardly into engagement with the second valve member to open the second valve member and thus permit flow in a forward direction through the assembly. In the event of reverse flow through the valve assembly, as might occur, for example, when more than one fluid source is connected to a length of tubing, the second valve member moves upwardly against a second valve seat therefor to prevent reverse flow beyond the valve assembly.

The double seating action obtained by the use of multiple valve members to prevent or control flow in a first direction insures positive shut-off of flow and significantly reduces or even eliminates the problem of leakage of fluid past the valve members, as might occur if a single valve member is used, as in prior art constructions, and particulate material becomes trapped between the single valve member and its seat or the valve member itself is imperfect. Additionally, the unique structure of the dual valve assembly of the invention provides a means for preventing reverse flow through the valve assembly without requiring expensive and power consuming multiple valve control members. Also, the unique dual valve assembly of the invention is completely automatic in operation and does not require the presence of an attendant or the like to manipulate the valves in order to prevent backflow of fluid through the system when multiple fluid sources are used, or to switch from one fluid source to another, as is necessary in prior art devices.

OBJECTS OF THE INVENTION

Accordingly, it is an object of this invention to provide a valve assembly for controlling forward and reverse flow through a flow line wherein the valve assembly includes multiple valve members seating in a first direction against respective valve seats to insure positive shut-off of flow in a first direction, and wherein one of the valve members has a second seat against which of the said one valve member engages to prevent reverse flow through the system.

Another object of the invention is to provide a valve means for controlling both forward and reverse flow through a valve assembly, wherein the valve means includes two valving members mounted in a valve body for movement toward and away from respective valve seats to control flow through the assembly in a first direction, and wherein motive means is operatively associated with one of the valve members for moving it away from its seat and an elongate valve actuating rod is extended between the two valve members such that when the first valve member is moved from its seat by the motive means, the rod engages the second valve member to move it from its seat, whereby flow is enabled through the assembly, and further wherein the second valve member is movable into engagement with a second valve seat to prevent reverse flow through the assembly.

A still further object of the invention is to provide a valve assembly for use in an intravenous administration set wherein more than one fluid is to be administered to a patient and wherein the valve means includes multiple valve members normally seated under the action of gravity and fluid pressure to prevent flow in a first direction from one of the fluid sources and wherein one of the valve members seats in a reverse direction to prevent reverse flow through the valve means from the other of said fluid sources.

DETAILED DESCRIPTION OF THE INVENTION

Figure 1:
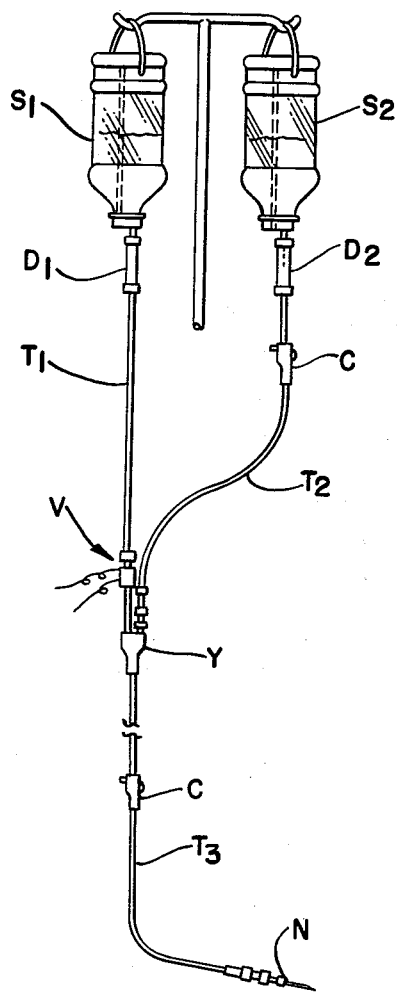
FIG. 1 is a fragmentary view in elevation of an IV set for controlling flow from a plurality of fluid sources and incorporating a valve in accordance with the invention.
Figure 2:
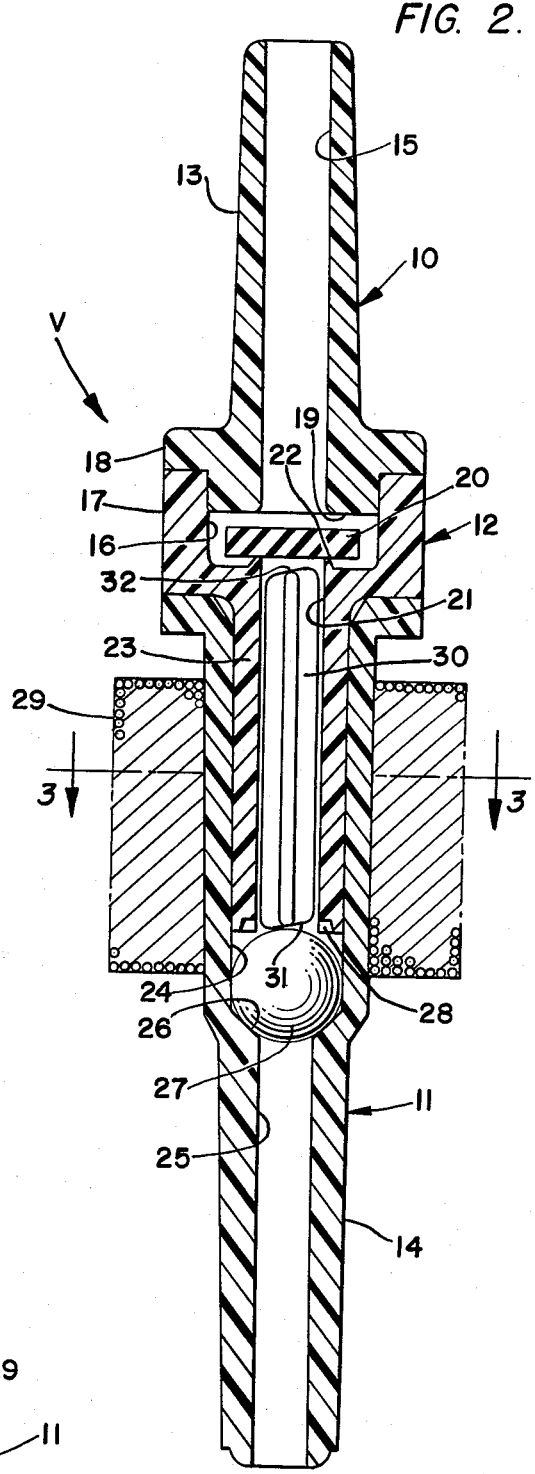
FIG. 2 is a greatly enlarged view in section of the valve assembly and actuator according to the invention.
Figure 3:
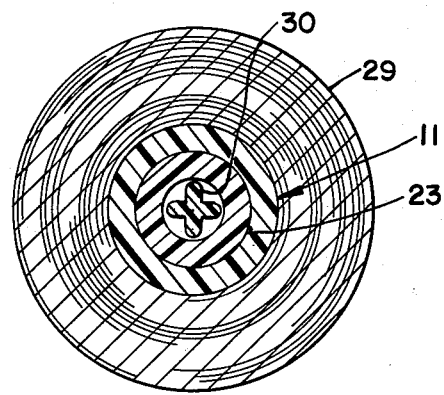
FIG. 3 is a view in section taken along line 3—3 in FIG. 2.

In the drawings, wherein like reference numerals indicate like parts throughout the several views, a first source S1 of fluid to be administered to a patient is connected with a drip chamber D1 which has a length of tubing T1 connected thereto and extending to a valve assembly V in accordance with the invention. The valve assembly V connects the length of tubing T1 to a Y-connector Y or the like which, in turn, has a length of tubing T3 connected therewith and extending to a cannula or needle N. A suitable flow control means such as a clamp C, or the like, is provided in the length of tubing T3 for controlling flow therethrough.

A second source of fluid S2 to be administered to a patient is supported adjacent the first source and has a drip chamber D2 associated therewith connected to a length of tubing T2 which joins the source S2 with the Y-connector Y for supplying the fluid to the length of tubing T3, and thus through the needle N to a patient or the like. A suitable clamp C is provided in the length of tubing T2 for controlling flow therethrough.

During normal use, the valve V is operated between open and closed positions by suitable control means (not shown) in a manner to effect a desired drip rate of fluid from the source S1 through the lengths of tubing T1 and T3 to a patient or the like. Under some circumstances it may be desired to administer the second fluid S2 either simultaneously with the fluid from source S1 or separately therefrom. In such event the clamp C in the length of tubing T2 is opened to enable flow of fluid from source S2 to the Y-connector Y and thence through the length of tubing T3 to the patient or the like. The valve V may in such instance be left de-energized whereby the fluid from the source S1 is not administered to the patient, or the valve V may continue to be energized at a predetermined frequency of operation to obtain a desired flow rate from the source S1, in addition to a desired flow rate of fluid from the source S2.

When the two sources S1 and S2 are connected with the common length of tubing T3, conditions may occur whereby the pressure of fluid in source S2 is greater than that in source S1 and thus resulting in backflow of fluid from source S2 through the connector Y and up through the valve V into tube T1. In order to prevent this occurrence, the valve assembly V is constructed as more specifically shown in FIGS. 2–5.

The valve assembly V comprises an inlet body portion 10, an outlet body portion 11, and an intermediate connecting body portion 12. The inlet and outlet body portions 10 and 11 have tapered fittings 13 and 14 thereon for connection to lengths of tubing or the like in a conventional manner. The inlet body portion 10 has an axial bore therethrough defining an inlet passageway 15 communicating at its inner end with a valve chamber 16 defined in the adjacent diametrically enlarged portion 17 of the intermediate valve body portion 12. A radially outwardly extending flange 18 is formed on the inner end of inlet body portion 10 and is suitably secured to the axial end surface of the diametrically enlarged portion 17 of intermediate body portion 12 in a suitable and conventional manner as by means of an adhesive or a sonic weld or the like. Additionally, the inner end surface of the inlet body portion 10 defines a valve seat 19 thereon for cooperation with a disc-shaped valve member 20 reciprocable in the valve chamber 16 defined in the diametrically enlarged end portion of intermediate body portion 12.

The intermediate body portion 12 also has an elongate passageway 21 extended therethrough terminating at its upper end in an annular upstanding valve seat 22 on which the disc 20 is normally seated. The valve seat 22 presents a small cross-sectional area to the valve disc 20, whereby increased head and seat pressure is obtained to reduce the chance of leakage occurring between the valve disc and its seat 22. The passage 21 is formed in a downwardly projecting tubular extension 23 which is secured in any suitable manner, such as by means of an adhesive or sonic weld or the like in a bore 24 formed in the upper end of outlet body portion 11. The bore through the outlet body portion 11 is reduced in diameter at the outlet end 25 thereof and defines a tapered, upwardly facing shoulder 26 defining a valve seat for a valve ball member 27 reciprocable between the seat 26 and stop shoulders 28 formed on the lower end of the projection 23 of intermediate body portion 12. Electromagnet means 29 is disposed adjacent the valve ball 27 and cooperates therewith to move the valve ball 27 upwardly from its seat 26 when the electromagnet means 29 is energized. When the electromagnet means 29 is de-energized, the valve ball 27 returns to its seat 26 under the action of gravity and fluid pressure thereabove.

Figure 4:
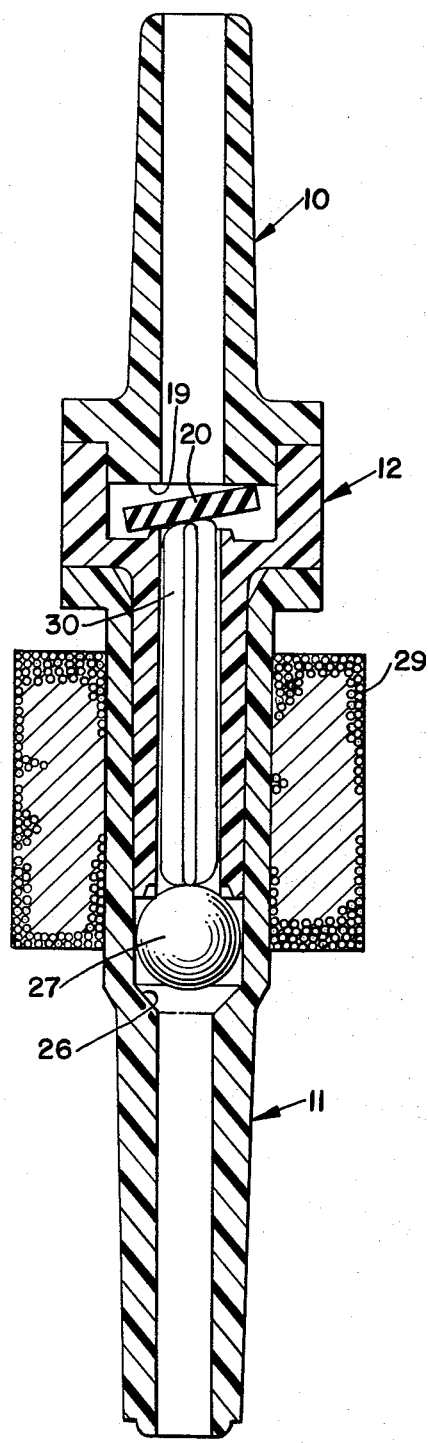
FIG. 4 is a view similar to FIG. 2 showing both of the valves in an open position for enabling flow in a forward direction through the assembly.
Figure 5:
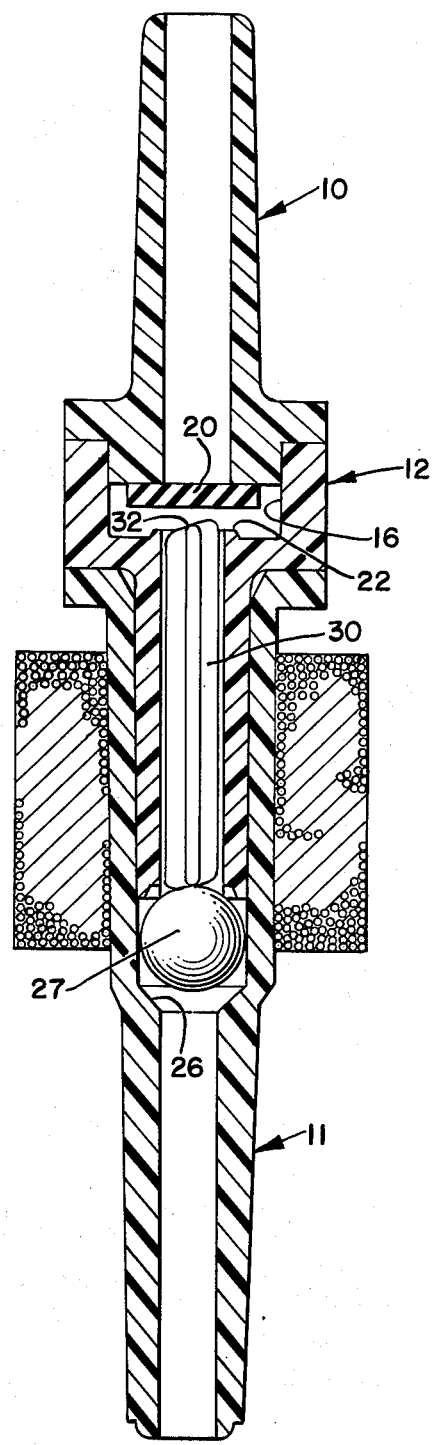
FIG. 5 is a view similar to FIG. 2 showing the second valve closed against its second seat to prevent reverse flow through the assembly.

An elongate axially fluted valve actuating rod 30 having parallel inclined opposite end surfaces 31 and 32 thereon is reciprocably received in the passage 21 through tubular extension 23 of intermediate body portion 12 and normally rests at its lower end 31 on the valve ball 27. Accordingly, when the electromagnet means 29 is energized, and the valve ball 27 is urged upwardly into engagement with the stops 28, the actuating rod 30 moves a corresponding distance bringing the tapered upper end surface 32 into engagement with the underside of disc 20, as seen in FIG. 4, and tilting the disc 20 upwardly from its valve seat 22, thereby enabling flow from the source S1 through the valve assembly V and to the tubing T3 or to a patient and the like.

In the event the pressure of fluid at source S2 exceeds that at source S1, for example, and fluid attempts to flow in a reverse direction through the valve assembly V, the disc 20 will be moved upwardly thereby against its upper valve seat 19, thereby precluding reverse flow through the valve assembly V.

Thus, with the present invention the valve ball 27 is lifted from its seat in a normal manner by the electromagnet means 29, and when the ball moves upwardly, it moves the valve actuating rod 30 upwardly into engagement with the disc valve 20 to open the disc valve 20. As seen in FIG. 4, the tapered upper end surface 32 of the valve actuating rod 30 results in the disc 20 being opened in an oblique manner, resulting in a mechanical advantage and thereby requiring less force to open the disc valve 20. After a drop is detected, the electromagnet means is de-energized and the disc valve 20 closes first against its seat and the valve ball 27 then closes against its seat. The provision of two valves in the unique valve assembly V results in two sealing surfaces being provided as compared to one sealing surface in conventional valve constructions, thus insuring that a liquid-tight closure will be obtained and eliminating the problem of leakage through the valve. Moreover, the flat disc valve 20 takes full advantage of the hydraulic pressure available, in that all forces are perpendicular to the disc urging it against its seat. In this connection, its seat 22 presents a small seating surface or area whereby a relatively high valve to seat pressure is produced. Less area for buildup of dirt and the like is also provided by this arrangement. Additionally, the unique valve actuating rod 30 enables precise finite control over the valve opening movement, in that a predetermined movement of the valve ball 27 results in a predetermined lesser movement of the valve disc 20.

The provision of the second valve seat 19 for the valve disc 20 also eliminates the need for hold down magnets or the like for the valve ball 27 to prevent reverse flow through the assembly.

The elements comprising the valve assembly may be made of any suitable material compatible with the fluids and chemicals likely to be encountered and possessing the necessary properties for the intended use. The valve disc 20, for example, is preferably made of rubber or a similar material, and the valve ball 27 is preferably made of steel or the like.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A dual valve assembly for use in intravenous administration from multiple parenteral fluid sources, said valve assembly controlling flow of fluid in forward and reverse directions therethrough, comprises a valve body having an inlet and an outlet and defining first and second spaced apart valve chambers therein, a first valve member is movable in the first valve chamber between a valve seat and a valve stop, a second valve member is movable in the second valve chamber between spaced opposed valve seats, and means extends between the first valve member and the second valve member to engage the second valve member and move it from one of its seats in response to movement of the first valve member from its seat, whereby flow is enabled from the inlet to the outlet, said second valve member being movable by fluid pressure into closing engagement with the other of its seats in response to flow from the outlet toward the inlet to preclude reverse flow through the assembly.

2. A dual valve assembly as in claim 1, wherein valve operating means is operatively associated with the first valve member to move it to its open position.

3. A dual valve assembly as in claim 2, wherein the first valve member comprises a ferromagnetic material and the valve operating means comprises an electromagnet positioned externally of the valve body.

4. A dual valve assembly as in claim 1, wherein the inlet, outlet and valve seats are coaxially arranged and the first and second valve members are in alignment with one another in the valve body.

5. A dual valve assembly as in claim 4, wherein the means extending between the first valve member and the second valve member comprises an elongate rod normally engaged with the first valve member and movable therewith when the first valve member moves from its seat to engage the second valve member and move it from its said one seat.

6. A dual valve assembly as in claim 5, wherein the rod is normally spaced from the second valve member so that the first valve member opens before the second valve member opens.

7. A dual valve assembly as in claim 4, wherein the second valve member comprises a disc of elastomeric material and its said one seat comprises an annular, raised projection presenting a small area of contact with the valve disc to thus increase the contact pressure between the disc and seat.

8. A dual valve assembly as in claim 6, wherein the end of the rod engageable with the disc valve member is tapered and engages the disc off-center to cause the disc to open obliquely, thereby obtaining a mechanical advantage of the opening movement of the disc.

9. A dual valve assembly as in claim 6, wherein the second valve member is spaced from the rod when the second valve member is engaged with its said other seat and said second valve member closes on its said one seat prior to the closing of the first valve member on its seat.

10. A dual valve assembly as in claim 1, wherein a length of flexible intravenous tubing is connected at one end with the inlet of the valve assembly and is connected at its other end with a first source of fluid to be administered to a patient, the outlet of the valve assembly being connected with a further length of intravenous tubing.

* * * * *